(12) United States Patent
Horsch

(10) Patent No.: US 11,426,521 B2
(45) Date of Patent: Aug. 30, 2022

(54) PHARMACEUTICAL CONTAINER AND LIQUID COMPOSITION

(71) Applicant: SCHOTT Schweiz AG, St. Gallen (CH)

(72) Inventor: Elmar Horsch, Schwellbrunn (CH)

(73) Assignee: SCHOTT Schweiz AG, St. Gallen (CH)

(*) Notice: Subject to any disclaimer, the term of this patent is extended or adjusted under 35 U.S.C. 154(b) by 226 days.

(21) Appl. No.: 16/816,950

(22) Filed: Mar. 12, 2020

(65) Prior Publication Data
US 2020/0289759 A1 Sep. 17, 2020

(30) Foreign Application Priority Data

Mar. 15, 2019 (EP) .................................... 19163313

(51) Int. Cl.
*A61M 5/31* (2006.01)
*A61J 1/06* (2006.01)

(52) U.S. Cl.
CPC ............ *A61M 5/3129* (2013.01); *A61J 1/062* (2013.01); *A61M 2005/3131* (2013.01); *A61M 2205/0238* (2013.01)

(58) Field of Classification Search
CPC ........ A61M 5/3129; A61M 2005/3131; A61M 2205/0238; A61M 2005/3143; A61M 5/31513; A61M 2205/0222; A61J 1/1468
See application file for complete search history.

(56) References Cited

U.S. PATENT DOCUMENTS

| 6,461,334 | B1 | 10/2002 | Buch-Rasmussen et al. |
| 2012/0165755 | A1 | 6/2012 | Chattaraj et al. |
| 2015/0119817 | A1 | 4/2015 | Prasad et al. |
| 2018/0117260 | A1* | 5/2018 | Shluzas ............ A61M 5/28 |
| 2018/0243508 | A1* | 8/2018 | Berg ............ A61M 5/31505 |
| 2020/0164152 | A1* | 5/2020 | Hetting ............ A61M 5/31515 |
| 2020/0410897 | A1* | 12/2020 | Baker ............ A61M 5/31501 |

FOREIGN PATENT DOCUMENTS

| WO | 2016/039816 A1 | 3/2016 |
| WO | 2018/157097 A1 | 8/2018 |

OTHER PUBLICATIONS

European Search Report dated May 14, 2019 for European Patent Application No. 19 16 3313 (4 pages).
European Office Action dated Jun. 7, 2019 for European Patent Application No. 19 163 313 (7 pages).

* cited by examiner

*Primary Examiner* — Lauren P Farrar
(74) *Attorney, Agent, or Firm* — Taylor IP, P.C.

(57) ABSTRACT

A pharmaceutical container for drug delivery includes a barrel configured to slidably receive a stopper. The container exhibits a ratio of a break loose force (BLF) relative to a glide force (GF) of BLF/GF≤2 during a break loose and glide force test and a total glide force variation $TGFV=GF_{max}-GF_{min}$ measured when the stopper is moved from a start position to its end position is TGFV<2 N.

22 Claims, 8 Drawing Sheets

PHARMACEUTICAL CONTAINER AND LIQUID COMPOSITION

CROSS REFERENCE TO RELATED APPLICATIONS

This application claims priority to European Patent Application EP 19163313.0 filed on Mar. 15, 2019, which is incorporated herein by reference.

BACKGROUND OF THE INVENTION

1. Field of the Invention

The present invention relates to pharmaceutical containers for drug delivery, and liquid compositions.

2. Description of the Related Art

Pharmaceutical containers for drug delivery are as such known in the prior art. These containers usually feature a stopper useful for eluting the contents of the container through an outlet. The stopper must slide within the container.

In most of these containers, the stopper is moved from a proximal start position to a distal end position using finger force. Finger force is limited so that the force needed to remove the stopper from its start position (break loose force) cannot be too high. Also it cannot be too low so that the stopper is not moved accidentally before the intended application of the drug. Further, the force needed to move the stopper from its start position to its end position (glide force) should not be too high for the same reasons.

Generally, very low break loose and glide force values can be achieved by choosing a stopper with a very small outer diameter relative to the container's inner diameter. However, if the stopper's outer diameter is too small, it will not seal the container sufficiently so that the contents of the container, i.e., the drug composition, might leak past the stopper.

WO 2018/157097 A1 teaches stoppers for pharmaceutical containers. The stoppers have very large outer diameters relative to the container's inner diameter in order to achieve adequate sealing of the container. The stoppers taught in this prior art document have to be plasma treat-ed or autoclaved to achieve adequate break loose and glide forces, which includes increased production costs. Further, the strong compression needed to set the stopper into the container increases the risk of tilting the stopper within the container so that production processes may be interrupted.

What is needed in the art is pharmaceutical containers that overcome at least some of the drawbacks of the prior art.

SUMMARY OF THE INVENTION

In some exemplary embodiments provided according to the invention, a pharmaceutical container for drug delivery includes a barrel configured to slidably receive a stopper. The pharmaceutical container exhibits a ratio of a break loose force (BLF) relative to a glide force (GF) of BLF/GF≤2 during a break loose and glide force test and a total glide force variation $TGFV=GF_{max}-GF_{min}$ measured when the stopper is moved from a start position to its end position is TGFV<2 N. The stopper has a proximal end suitable for contacting a plunger rod, a distal end suitable for contacting a pharmaceutical composition, a circumferential surface at least partially suitable for contacting an inner surface of the barrel, and one or more annular protrusions contacting the inner surface of the barrel when the stopper moves in a distal direction, the one or more annular protrusions each having a rising edge and a falling edge in a proximal-distal direction. The rising edge of a most proximal annular protrusion and the inner surface of the barrel span angle X in the distal direction, the falling edge of a most distal annular protrusion and the inner surface span an angle A in a proximal direction, and the ratio X/A is at least 1.05.

In some exemplary embodiments provided according to the invention, a pharmaceutical container for drug delivery includes a barrel configured to slidably receive a stopper. The pharmaceutical container exhibits a ratio of a break loose force (BLF) relative to a glide force (GF) of BLF/GF≤2 during a break loose and glide force test and a total glide force variation $TGFV=GF_{max}-GF_{min}$ measured when the stopper is moved from a start position to its end position is TGFV<2 N.

In some exemplary embodiments provided according to the invention, method of treatment includes administering to a subject an effective amount of an active ingredient using a pharmaceutical container. The pharmaceutical container includes a barrel configured to slidably receive a stopper. The pharmaceutical container exhibits a ratio of a break loose force (BLF) relative to a glide force (GF) of BLF/GF≤2 during a break loose and glide force test and a total glide force variation $TGFV=GF_{max}-GF_{min}$ measured when the stopper is moved from a start position to its end position is TGFV<2 N. The stopper has a proximal end suitable for contacting a plunger rod, a distal end suitable for contacting a pharmaceutical composition, a circumferential surface at least partially suitable for contacting an inner surface of the barrel, and one or more annular protrusions contacting the inner surface of the barrel when the stopper moves in a distal direction, the one or more annular protrusions each having a rising edge and a falling edge in a proximal-distal direction. The rising edge of a most proximal annular protrusion and the inner surface of the barrel span angle X in the distal direction, the falling edge of a most distal annular protrusion and the inner surface span an angle A in a proximal direction, and the ratio X/A is at least 1.05.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
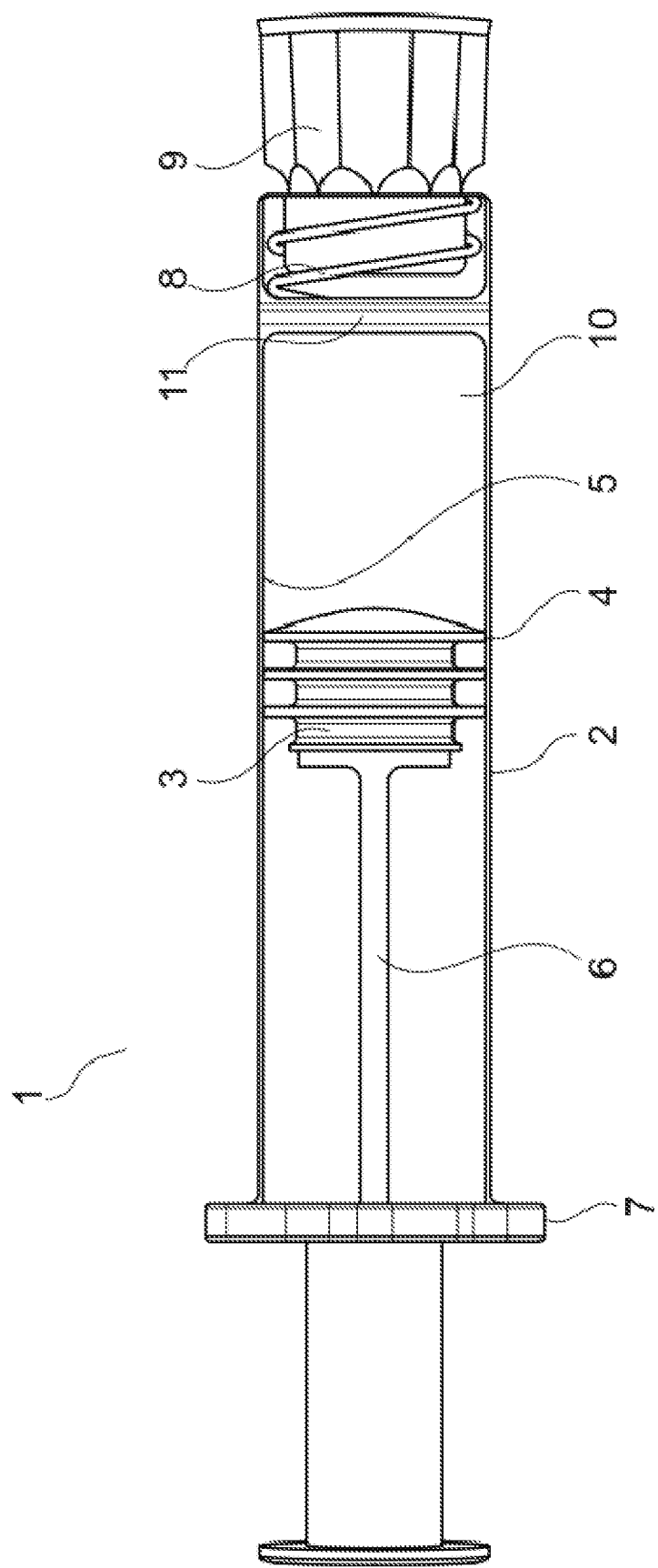
FIG. 1 illustrates a pharmaceutical container of the prior art.

In some exemplary embodiments, pharmaceutical containers for drug delivery include: a barrel and a stopper, the stopper being slidably arranged within the barrel, the stopper having a proximal end suitable for contacting a plunger rod, and a distal end suitable for contacting a pharmaceutical composition, the stopper having a circumferential surface partially contacting an inner surface of the barrel, the stopper having one or more annular protrusions contacting the inner surface of the barrel when the stopper moves in a distal direction, and the annular protrusions each having a rising edge and a falling edge in a proximal-distal direction.

The proximal-distal direction is equivalent to the direction of a vector pointing from the proximal end to the distal end. The rising edge of the most proximal annular protrusion and the inner surface of the barrel span angle X in the distal direction, the falling edge of the most distal annular protrusion and the inner surface span an angle A in the proximal direction, and the ratio X/A may be at least 1.05.

The container may exhibit a ratio of the break loose force (BLF) relative to the glide force (GF) of BLF/GF≤2 during a break loose and glide force (BLGF) test. It was found that controlling the ratio of BLF and GF is important because if the BLF is too high compared to GF, the user of the container will have to push very hard to remove the stopper from its start position so that the stopper might be pushed too fast all the way to the end position after the stopper breaks loose. Keeping the ratio BLF/GF in a balanced range, will facilitate a controlled drug delivery without unnecessary pain for the patient. Also, the risk of leakage of the contents of the container will be smaller, if the acceleration of the stopper is limited after breaking loose. The ratio BLF/GF may be >1. It is an aspect of some embodiments disclosed herein to keep the BLF/GF ratio essentially constant even after storage of the container during administration.

The total glide force variation $TGFV = GF_{max} - GF_{min}$ measured when the stopper is moved from start position to its end position may be TGFV<2 N. It is important to control TGFV because the difference between maximum GF and minimum GF will strongly influence the user's ability to dose the drug composition stored in the container adequately.

In some embodiments, pharmaceutical containers for drug delivery having a barrel configured to slidably receive a stopper are the provided. The container exhibits a ratio of the BLF relative to the GF of BLF/GF≤2 during a BLGF test and the total glide force variation $TGFV = GF_{max} - GF_{min}$ measured when the stopper is moved from start position to its end position is TGFV<2 N. The test stopper has a proximal end suitable for contacting a plunger rod and a distal end suitable for contacting a pharmaceutical composition, a circumferential surface at least partially suitable for contacting the inner surface of the barrel, one or more annular protrusions contacting the inner surface of the barrel when the stopper moves in distal direction, and the annular protrusions each having a rising edge and a falling edge in proximal-distal direction. The rising edge of the most proximal annular protrusion and the inner surface of the barrel span angle X in the distal direction, the falling edge of the most distal annular protrusion and the inner surface span an angle A in the proximal direction, and the ratio X/A is at least 1.05.

The BLF, the GF and the BLGF can be measured according to the method described further herein as the BLGF test.

The Angles X, a and their Ratio X/A

The rising edge of the most proximal annular protrusion and the inner surface of the barrel span angle X which opens in the distal direction, the falling edge of the most distal annular protrusion and the inner surface span an angle A opening in the proximal direction. A "rising edge" in the context of this invention is an edge of an annular protrusion that extends in the direction of the inner surface of the barrel, when the stopper is inserted in the barrel, following the circumferential surface of the stopper in proximal-distal direction. A "falling edge" is an edge of an annular protrusion that extends in the direction towards the central longitudinal axis of the barrel, when the stopper is inserted in the barrel, following the circumferential surface of the stopper in proximal-distal direction.

In some embodiments, the ratio X/A is from >1.1 to 1.7. If the ratio of X/A is at least 1.05, the BLGF values are improved. In some embodiments, the ratio X/A is at least 1.1, such as at least 1.15, at least 1.2, or at least 1.25. The ratio may be limited to up to 1.7, such as up to 1.65, up to 1.6, up to 1.55, up to 1.5, or up to 1.45.

The angles X and/or A may be from >90° to <180°. In some embodiments, A is from 130° to 170°. The minimum value of A may be at least 100°, such as at least 110°, at least 120° or at least 130°. The upper limit of A may be 170°, 160°, 150° or 140°. X may be from 131° to 175°. The minimum value of X may be at least 101°, such as at least 111°, at least 121° or at least 131°. The upper limit of X may be 170°, 160°, 150° or 140°.

Keeping the angles and their ratio within appropriate ranges will contribute to solving the problem underlying this invention. Particularly, if angle X is too small, the ratio BLF/GF will increase. With the related angle ratio, the force inserted by a plunger rod needs to be distributed and shared inside the plunger towards the sealing lips in a uniform and controlled way, which can be imagined by strength lines and the uncontrolled deformation of the plunger can be avoided by the mentioned ratio of the design angles.

Annular Protrusions

The stopper may have at least two annular protrusions. In some embodiments, the stopper has from one to five annular protrusions, such as from two to four annular protrusion. In some embodiments, the stopper may have one, two, three, four or five annular protrusions. Annular protrusions are useful for closing the juncture between inner surface of the barrel and the stopper's circumferential surface. The stopper's diameter is greater at the annular protrusions than the average diameter of the stopper. The annular protrusions contact the inner surface of the barrel when the stopper is moved in distal direction, e.g., when the stopper is used to push the contents of the pharmaceutical container out of the container. The surfaces of the annular protrusions form part of the circumferential surface of the stopper.

At least one, and in some embodiments all, of the annular protrusions may have a diameter that exceeds the inner diameter of the barrel. The diameter of at least one or all of the annular protrusions exceed the inner diameter of the barrel by at least 0.05 mm, or at least 0.1 mm, or at least 0.15 mm. The outer diameter of the annular protrusion may be equivalent to the outer diameter of the stopper. The diameter is measured perpendicular to the barrel's longitudinal axis.

Surface Roughness

Surface roughness values can, for example, be controlled by adjusting the temperature during injection molding. In some embodiments, the inner surface of the barrel may have a surface roughness Ra of less than 100 nm. The surface roughness Ra indicated herein may be an average, or a maximum surface roughness. In some embodiments, the surface roughness Ra of the inner surface of the barrel is less than 80 nm, such as less than 70 nm, less than 60 nm, less than 50 nm or less than 40 nm. The surface roughness Ra may be at least 1 nm, at least 3 nm or at least 7 nm. Exemplary ranges include surface roughness Ra values from 1 nm to 80 nm, from 3 nm to 70 nm, or from 7 nm to 50 nm.

Surface roughness can additionally or alternatively be given as Rms roughness. In some embodiments, the inner surface of the barrel may have a surface roughness Rms of less than 150 nm. The surface roughness Rms indicated herein may be an average, or a maximum surface roughness. In some embodiments, the surface roughness Rms of the inner surface of the barrel is less than 120 nm, such as less than 100 nm, less than 80 nm, less than 70 nm or less than 60 nm. The surface roughness Rms may be at least 2 nm, at least 5 nm or at least 8 nm. Exemplary ranges include surface roughness Ra values from 2 nm to 120 nm, from 5 nm to 100 nm, or from 8 nm to 60 nm. Surface roughness influences the stopper's ability to move while contacting the barrel's inner surface. For example, the coefficient of friction may be very high, if surface roughness is very high.

The surface roughness of the inner surface of the barrel may decline from the stopper's start position to its end position by at least 3% Ra and/or Rms relative to the roughness value at the start position. In some embodiments, the surface roughness Ra declines from start to end position of the stopper by at least 5%, at least 7%, by at least 10%, at least 20%, at least 30%, at least 40%, at least 50%, at least 60% or at least 70%. The surface roughness Rms may decline from start to end position of the stopper by at least 5%, at least 7%, by at least 10%, at least 20%, at least 30%, at least 40%, at least 50%, at least 60% or at least 70%.

The stopper's start position is the position where the stopper is located within the barrel before the container is used for drug delivery. In some embodiments, the pharmaceutical container is a pre-filled syringe. In a pre-filled syringe the start position is the location of the stopper before use. This will usually be the most proximal position of the stopper. The stopper's end position is the position where the stopper is located after pushing the nominal volume of the container out of the barrel, e.g., when the stopper touches the distal end of the barrel. The stopper's start position may be located within a distance of up to 20% of the container's length from its proximal end. The end position may be located within a distance of from 80% to 100% of the container's length from its proximal end.

The inner surface of the barrel may have a surface roughness distribution such that the surface roughness measured at the start position SP, a middle position MP, and an end position EP is as follows, wherein the middle position may be located halfway between start and end position:
SP 100%
MP 40 to 60%
EP 20 to 35%.

Controlling the surface roughness may contribute to a very low TGFV. Surface roughness can be controlled by adjusting production parameters like melt temperatures, molding times and polymer blends, or by surface treatment like coating or plasma treatment. The pharmaceutical containers may be made by injection molding. Injection molding requires the container to be at least slightly conical, i.e., the inner diameter of the barrel will decrease from start to end position. Thus, compression of the stopper increases from start to end position so that $GF_{max}$ would increase and TGFV will increase as well. Within this description, any reference to the "inner diameter" of the barrel means the maximum inner diameter of the barrel, unless otherwise indicated.

The described surface roughness distribution may be achieved, for example, by positioning the injection nozzle closer to the end position than to the start position during injection molding so that the polymer melt temperature is higher at the end position than at the start position during injection. Or the mold temperature may be influenced by segmental heating and/or cooling to create a temperature gradient in the barrel direction.

The surface roughness values can be measured using a white light interferometer according to DIN EN ISO 25178-2:2012, DIN EN ISO 25178-6:2010 and DIN EN ISO 25178-604:2013-12 (together with DIN EN ISO 4288:1998 and DIN EN ISO 3274:1998).

Stopper

The stopper has a body having at least one annular protrusion, and a circumferential surface. The "circumferential surface" is the surface of the stopper that faces towards the inner surface of the barrel when the stopper is disposed in the barrel. The circumferential surface includes the surface of annular protrusions. If the stopper is coated, the surface of the coating that faces the inner surface of the barrel is part of or constitutes the circumferential surface. The "contact surface" is the part of the circumferential surface that touches the inner surface of the barrel when the stopper is inserted in the barrel.

An "annular protrusion" is a portion of the stopper that has a greater than average diameter, measured perpendicular to the longitudinal axis of the barrel. The annular protrusions touch the inner surface of the barrel so as to seal the junction between stopper and barrel. Any portion of the stopper having a greater than average diameter, but not touching the inner surface of the barrel to an extent of at least 80%, 90%, 99.9% or 100% during movement of the stopper in distal direction is not considered an "annular protrusion". Annular protrusions help keeping the stopper in the intended position within the barrel, stabilize its orientation in the proximal-distal direction, and thereby influence the BLF and GF values of the container. Further, the annular protrusions seal the junction between stopper and inner surface of the barrel.

The stopper may optionally feature one or more trailing ribs. A "trailing rib" is a portion of the stopper that has a greater than average diameter, measured perpendicular to the longitudinal axis of the barrel. However, the trailing rib has a smaller diameter than an annular protrusion so that it does not touch the barrel's inner surface to a significant extent, when the stopper is moved in the proximal-distal direction. Such trailing ribs may serve the purpose of stabilizing the stoppers orientation within the barrel, without effectively sealing the junction between stopper and inner surface. Trailing ribs do not usually significantly influence BLF and GF because their contact with the inner surface is limited, if any.

The stopper may be coated with a coating. The coating may be a polymer. In some embodiments, the coating comprises a resin, such as a fluorinated polymer such as a polymer selected from the group consisting of polytetrafluoroethylene (PTFE), densified expanded polytetrafluoroethylene (ePTFE), tetrafluoroethylene (TFE), tetrafluoroethylene-perfluoroethylene copolymer, tetrafluoroethylene-hexafluoropropylene copolymer, tetrafluoroethylene-ethylene copolymer, trichlorotrifluoroethylene, polyvinylidene fluoride, polyvinyl fluoride, perfluoropropylvinylether, perfluoroalkoxy polymers, as well as copolymers, blends and combinations thereof. The coating may also be formed by layers comprising polyethylene, polypropylene, polyparaxylxylene, polylactic acid, as well as copolymers, blends and combinations thereof. A PTFE coating is an exemplary coating option. These coatings reduce the coefficient of friction of the stopper's circumferential surface on the inner surface of the barrel. In some embodiments, at least the parts of the stopper's circumferential surface that are supposed to be in contact with the barrel's inner surface will be coated.

The stopper may have an elastomeric body with an at least 10 MPa yield stress measured according to ISO 527-2:2012 (E) and/or a low coefficient of sliding friction below 0.23 against steel measured according to DIN EN ISO 8295/2004-10. The stopper may be made of thermoplastic elastomers and/or rubbers, such as natural or synthetic rubbers. Suitable rubber materials may be selected from the group consisting of butyl rubbers, halogenated butyl rubbers, acrylonitrile-butadiene rubbers, isoprene rubbers, neoprene rubbers, butadiene rubbers, styrene-butadiene rubbers, ethylene-propylene rubbers, isoprene-isobutylene rubbers, nitrile rubbers, and combinations and mixtures thereof. The body of the stopper may be made of the above-listed rubbers and/or thermoplastic elastomers.

The body may be coated with a resin as described previously. The coating may have a thickness of less than 1 mm, such as from 0.5 µm to 200 µm, from 10 µm to 125 µm, or from 30 to 100 µm. These thicknesses have been proven to be easily applied and sufficient for the desired effect on the friction.

The circumferential surface of the stopper may have a water contact angle of at least 100°, or even at least 110°. The circumferential surface of the stopper may be superhydrophobic. Using superhydrophobic stoppers in the containers described herein contributes to the beneficial BLGF values due to the low coefficient of sliding friction in combination of a low adhesion disposition.

The pharmaceutical containers described herein allow for excellent sealing between annular protrusions and inner surface of the barrel even at comparatively low compressions of the stopper. The stopper compression (SC) can be calculated as follows. SC=(OD−ID)/OD, with OD denoting the stopper's outer diameter and ID denoting the barrel's inner diameter. The stopper compression may be less than 0.1, less than 0.075, or even less than 0.05. Using a low stopper compression allows for easy gliding of the stopper within the barrel thereby keeping TGFV very low, and reducing BLF.

The circumferential surface of the stopper and the inner surface of the barrel may at least partially contact each other in a contact area. The contact area is sometimes also referred to as the "sealing area." In some embodiments, the contact area will be at least 8 mm$^2$ and at most 48 mm$^2$. The contact area may be 8-48 mm$^2$ or 10-40 mm$^2$, 15-30 mm$^2$, 16-24 mm$^2$. In the case of plural annular protrusions, each protrusion contributes to the contact area. A minimum contact area will be useful to achieve sufficient sealing. If the contact area is too high, BLGF values may increase too much.

Pharmaceutical Container

The pharmaceutical container may be selected from a syringe, a cartridge and a carpule.

The inner surface of the barrel may have a water contact angle of at least 80°. High water contact angles indicate that the inner surface is hydrophobic. If the water contact angle exceeds 90°, the surface is called superhydrophobic. In some embodiments, the inner surface of the barrel is superhydrophobic. Its water contact angle may be as high as at least 95°, or at least 100°. In some embodiments, the inner surface of the barrels are not plasma treated and/or otherwise hydrophilicity-increased. A typical plasma-treated inner surface will have a water contact angle significantly below 90°.

In some embodiments, the ratio of water contact angles between the stopper's circumferential surface $\theta_C$ and the barrel's inner surface $\theta_I$ is $\theta_C/\theta_I > 0.9$. In some embodiments, $\theta_C/\theta_I$ is from 0.9 to 2, or from >1 to 1.5. In some embodiments, said ratio $\theta_C/\theta_I$ is >1, >1.1 or >1.2. Controlling the water contact angle improves the BLGF properties. It was found that keeping the water contact angles of stopper and inner surface of the barrel within certain ranges helps achieving the desired properties.

The water contact angle can be measured according to DIN 55660-2:2011-12, chapter 5.2.2. using a static method with a drop volume of 2 µl.

The inner surface of the barrel may have a surface energy of less than 45 mN/m, or less than 40 mN/m. In some embodiments, the surface energy of the inner surface is higher than the surface energy of the circumferential surface of the stopper. The surface energy can be measured indirectly by calculating the value with the Owens-Wendt-Rabel-Kaelble (OWRK) method from contact angle measurements according to DIN 55660-2:2011-12, chapter 6.2.

The pharmaceutical container may be essentially lubricant-free. "Lubricant-free" means that the amount of lubricant per container is less than 100 µm, less than 30 µg, or even less than 10 µg. The above-mentioned limits may particularly apply to silicone as a lubricant.

The pharmaceutical container and/or the barrel may be partially or entirely made of a material suitable for pharmaceutical primary packaging. Suitable material includes glass or polymers. The polymers may be amorphous polymers. Transparent polymers may be used. Suitable polymers may be selected from the group comprising cyclic olefin copolymers (COC), cyclic olefin polymers (COP), polyethylene terephthalate (PET), polycarbonate (PC), polypropylene (PP), and methylmethacrylate acrylonitrile butadiene styrene polymer (MABS). These polymers have the advantage of low density, high transparency, low birefringence, extremely low water absorption, excellent water vapor barrier properties, high rigidity, strength and hardness, excellent biocompatibility, very good resistance to acids and alkalis, and very good melt processability.

The barrel and/or the pharmaceutical container may be made of polymer. In some embodiments, a polymer is chosen that has low density compared to glass, such as a density of from 0.9 to 1.2 g/cm$^3$, such as >1 to 1.1 g/cm$^3$. Transport costs can be reduced if low density material is used. The density may be determined using the method described in ISO 1183-1:2013-04.

For long term storage, a material may be used for the barrel that has a water vapor permeability of less than 0.1 g*mm/m$^2$*d, such as less than 0.07 g*mm/m$^2$*d or even less than 0.05 g*mm/m$^2$*d. Water vapor permeability may be tested using the method described in ISO 15106-3:2003.

In order for the BLF and GF to remain sufficiently constant over a temperature range relevant for biological active agents, such as from 4° C. to 25° C., the coefficient of linear thermal expansion (CTE) of the material used for the barrel may be within a range of from 0.3 to 0.8*10$^{-4}$ K$^{-1}$, or from 0.4 to $0.7*10^{-4}$ $K^{-1}$, or from 0.3 to $0.8*10^{-4}$ $K^{-1}$. In some embodiments, the ratio of the CTE of the material of the stopper and the material of the barrel, $CTE_S/CTE_B$, is less than 7, such as less than 6 or at most 5. If this ratio is too high, the stopper will contract significantly, when cooling the container to e.g. 4° C. in a refrigerator. This might cause leakage.

Exemplary embodiments provided according to the invention offer a large freedom of design because the effects of the invention may even be achieved by uncoated barrels. Hence, the inner surface of the barrel may be uncoated.

The barrel has an inner diameter ID measured perpendicular to the container's longitudinal axis. The inner diameter ID may range from 3 mm to 40 mm, such as from 4 mm to 20 mm. The inner diameter will generally be larger for larger barrel volumes. Larger diameters often correspond to greater BLF and GF values because of increased contact areas of the stopper's circumferential surface and the barrel's inner surface.

The wall of the barrel may be made of a transparent material. The transparent material may have a minimum transmission of at least 60% within a wavelength interval of at least 100 nm width within the wavelength range of 400 to 700 nm, measured at a thickness of the material of 1 mm. In some embodiments, the minimum transmission is at least 70%.

The material of the barrel wall may have a refractive index of from 1.5 to 1.6 and/or a diffraction characterized by an Abbe number of from 50 to 60. Using a material with adequate refractive index is useful to allow for good visual inspection of the contents of the pharmaceutical composition. The pharmaceutical container is suitable for administering parenteral drug compositions so that visual inspection of the container for impurities, precipitation, crystallization, and particles is of utmost importance.

The wall thickness of the barrel may be from 1 mm to 2.5 mm or from 1.2 mm to 2 mm or from 1.3 mm to 1.9 mm.

Liquid Composition

The invention also relates to liquid compositions for use in a method for treatment of the human or animal body by surgery or therapy, and/or for use in a diagnostic method practiced on the human or animal body. The liquid composition may be liquid and/or sterile. The pharmaceutical container may contain the liquid composition within the barrel.

The composition comprises at least one pharmaceutically active ingredient. "Pharmaceutically active ingredients" include therapeutic and/or diagnostic active ingredients.

The method includes administering to a subject an effective amount of said pharmaceutically active ingredient using the pharmaceutical container provided according to the invention.

The pharmaceutically active ingredient may be a peptide or protein, such as an antibody, an enzyme, a vaccine, a receptor or the like. The pharmaceutical container provided according to the invention is particularly suitable for administering biological active ingredients, such as peptides or proteins, since the container is very tolerant to temperature changes in terms of BLGF. This means that the BLGF does not vary significantly within a temperature range of from 4° C. to 25° C. This is relevant because biological agents will usually be stored in a refrigerator so as to increase the shelf life of the product.

In some embodiments, the pharmaceutically active ingredient is an immune inhibitory or anti-cancer agent. The active ingredient may be an immune checkpoint inhibitor or a TNFα antibody.

The pharmaceutical container may be combined with an injection device. The injection device may be attached to the container at the containers distal opening. The injection device may be a needle. The pharmaceutical container may be part of an auto-injector.

Break Loose and Glide Force

The pharmaceutical containers provided according to the invention may exhibit a maximum BLGF of not more than 12 N during a BLGF test. In some embodiments, the maximum BLGF may be limited to 9 N, 8 N, 7 N, 6 N, 5 N or even 4 N. The BLF may be at least 0.1 N or at least 0.5 N so as to avoid any unintended movement of the stopper.

In some embodiments, the maximum BLGF may correlate to the inner diameter of the barrel. In some embodiments, the ratio of maximum BLGF and the barrel's inner diameter ID is BLGF/ID<1 N/mm. In some embodiments, BLGF/ID may be at least 0.5 N/mm, or at least 0.6 N/mm. In some embodiments, BLGF/ID may be limited to ≤0.95 N/mm, ≤0.9 N/mm, ≤0.85 N/mm or ≤0.8 N/mm.

The container exhibits a ratio of the BLF relative to the GF of BLF/GF≤2 during a BLGF test. In some embodiments, the ratio of the BLF relative to the GF is characterized by BLF/GF≤3 even after accelerated aging for 105 days. In some embodiments, the ratio BLF/GF is <2, <1.8, <1.7, or even <1.5 for the containers provided according to the invention. In some embodiments, the ratio BLF/GF may be <2, <1.8, <1.7, or even <1.5 for the containers after accelerated aging for 105 days. In some embodiments, the relative difference in the ratios BLF/GF of aged containers (accelerated aging 105$d$), and non-aged containers (BLF/$GF_{105d}$-BLF/$GF_{0d}$)/BLF/$GF_{105d}$ is less than 10%, such as less than 5%.

The total glide force variation TGFV=$GF_{max}$-$GF_{min}$ measured when the stopper is moved from start position to its end position may be TGFV<2 N, <1.8 N or even <1.6 N. In some embodiments, the relative difference in the TGFV of aged containers (accelerated aging 105$d$), and non-aged containers ($TGFV_{105d}$-$TGFV_{0d}$)/$TGFV_{105d}$ is less than 40%, such as less than 35%.

The mean values of BLF and GF may be calculated using at least 12 containers, such as at least 15 containers. The mean BLF of the pharmaceutical containers provided according to the invention may be <9 N, <8 N, <7 N, <6 N, <5 N, <4 N, <3 N, or even <2 N. The mean GF of the pharmaceutical containers provided according to the invention may be <9 N, <8 N, <7 N, <6 N, <5 N, <4 N, <3 N, or even <2 N. In some embodiments, the relative difference in the BLF of aged containers (accelerated aging 105$d$), and non-aged containers ($BLF_{105d}$-$BLF_{0d}$)/$BLF_{105d}$ is less than 25%, <20%, <15%, <10% or even <5%. The relative difference in the GF of aged containers (accelerated aging 105$d$), and non-aged containers ($GF_{105d}$-$GF_{0d}$)/$GF_{105d}$ is less than 25%, <20%, <15%, <10% or even <5%.

Keeping the BLF and GF values within the ranges disclosed herein contributes to a sufficiently constant elution of liquid composition from the container during application. Particularly, if the BLF is much higher than the GF a large bolus may be eluted when the stopper breaks loose from the inner surface of the barrel. Also, if the GF is not sufficiently constant, the elution rate of liquid composition may vary.

"Accelerated aging" refers to an aging process where the respective containers are stored at 40° C. and 75% relative humidity. For example, some containers may be stored at these conditions for 105 days for comparison. Accelerated aging can be performed to estimate the influence of aging on the properties of the pharmaceutical containers provided according to the invention.

Break Loose and Glide Force Test

The BLGF test is conducted on a universal testing machine at room temperature, e.g. 23° C. A BLGF testing device with a 50 N test cup is used for this purpose. The samples were fixed in vertical orientation in a universal testing machine model 106, 2 kN from TesT AG, CH-6331 Hünenberg, Switzerland.

For this test plungers with flat ends, i.e., without any threads are used.

The BLF is the force needed to move the stopper from its original position. The GF is the force needed to keep the plunger moving after breaking it loose.

The pharmaceutical containers are filled with water for injection. After filling the specimens they are either stored or tested immediately, depending on the test purpose. The specimens are tested without needles.

The specimens are inserted into the holder and the pressure stamp is moved towards the plunger at a rate of 20 mm/min. Once a force of 0.25 N is measured the machine switches to the test rate of 100 mm/min and starts recording the data. The experiment ends when the measured force exceeds 35 N, which is usually the case when the distal end of the barrel is reached.

The BLF is the highest force measured within the first 4 mm of stopper movement. The mean and maximum GF values are measured within a test range starting after 4 mm of movement and ending 10 mm before reaching the distal end of the barrel.

Referring now to the drawings, FIG. 1 shows a pharmaceutical container 1. The pharmaceutical container comprises a barrel 2 and a stopper 3. The stopper 3 is slidably arranged within the barrel 2. The stopper 3 has a circumferential surface 4 partially contacting the inner surface 5 of the barrel 2. The stopper 3 is connected to a plunger rod 6. The pharmaceutical container further features a flange 7. At its distal end the container has threads 8 for mounting an injection device (not shown) or a cap 9. The pharmaceutical container may contain a liquid composition 10. The liquid composition 10 can be forced out of the barrel 2 by operation of the plunger rod 6. Pushing the plunger rod 6 into the barrel 2 will move stopper 3 in the direction of outlet 11. The stopper's distal end may have conical shape which may fit the shape of the barrel in the area of outlet 11. Throughout this description, "proximal" will be used to describe a location closer to the flange 7, whereas "distal" will be used to denote a location closer to the outlet 11.

Figure 2:
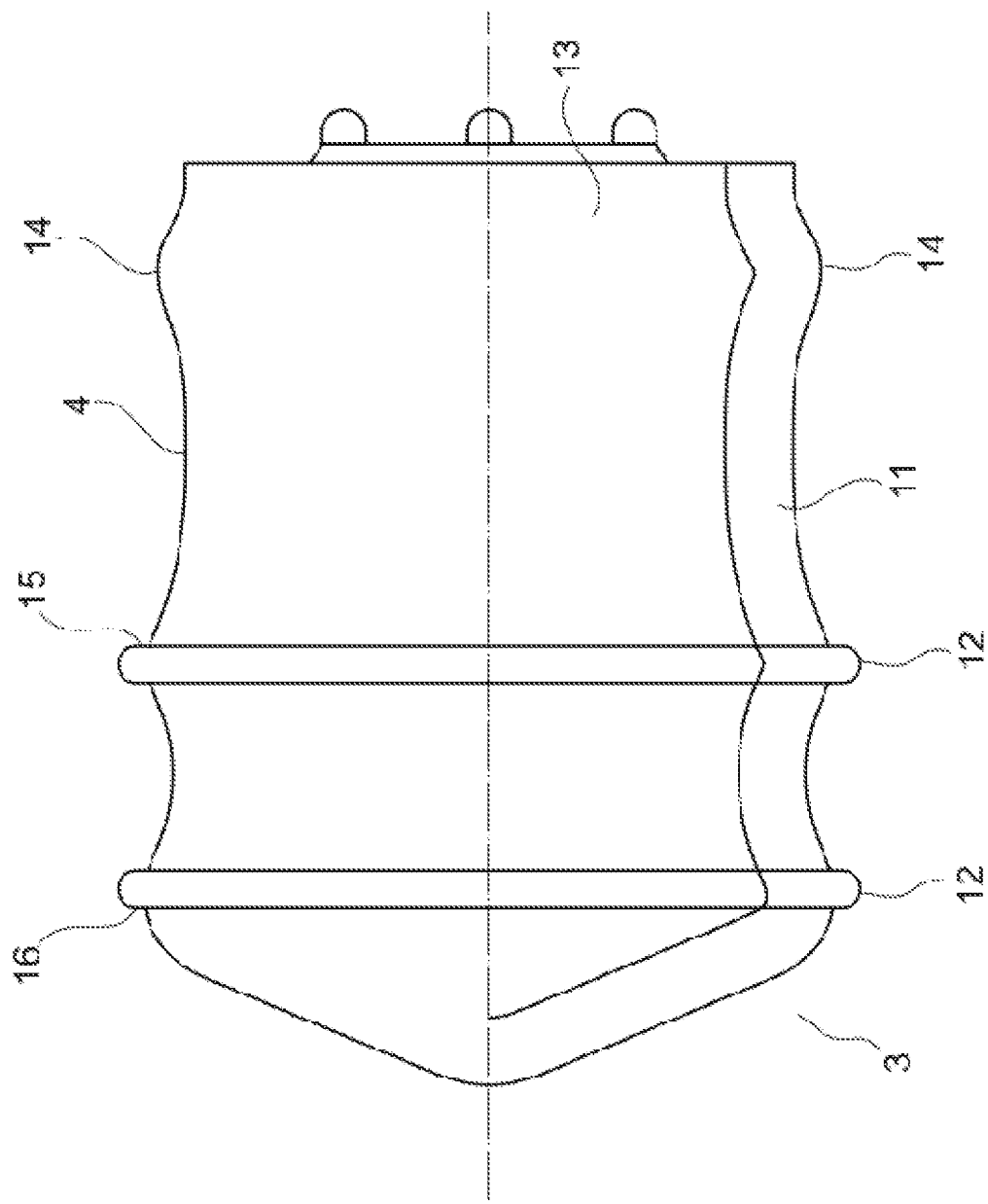
FIG. 2 illustrates a stopper as used in the prior art.

FIG. 2 shows a stopper 3 of the prior art. The stopper has a coating 11 that covers the stopper's body 13. The stopper also has annular protrusions 12 where the stopper's outer diameter is larger than the average outer diameter. The stopper shown in this figure has two annular protrusions having rising and falling edges. The rising edge 15 of the most proximal annular protrusion and the falling edge 16 of the most distal annular protrusion span the same angles (X/A=1) with an inner surface of a barrel (not shown). The stopper also has a trailing rib 14. The stopper has a smaller outer diameter in the location of the trailing rib 14 compared to the outer diameter in the location of the annular protrusions 12. When the stopper is moved within a barrel (not shown) in a distal direction, the trailing rib 14 will not touch the inner surface of the barrel. Therefore, it is not considered an annular protrusion according to the invention as it cannot influence break loose and glide forces.

Figure 3A:
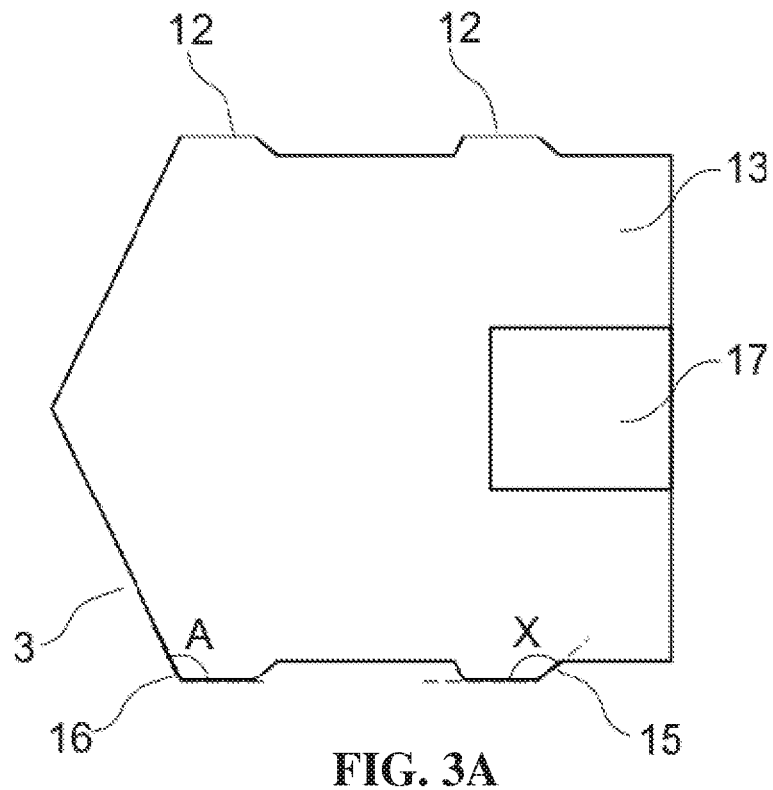
FIG. 3A illustrates a stopper as used according to an exemplary embodiment of this invention.

FIG. 3A shows a stopper 3 provided in accordance with the invention. The stopper has two annular protrusions 12, wherein the rising edge 15 of the most proximal annular protrusion and an inner surface of the barrel (not shown) will span angle X in the distal direction, and the falling edge 16 of the most distal annular protrusion and the inner surface span angle A in the proximal direction, when this stopper is disposed in a barrel of the pharmaceutical container. The ratio X/A is at least 1.05. The stopper body 13 comprises a receptacle 17 with threads for insertion of a plunger rod (not shown).

Figure 3B:
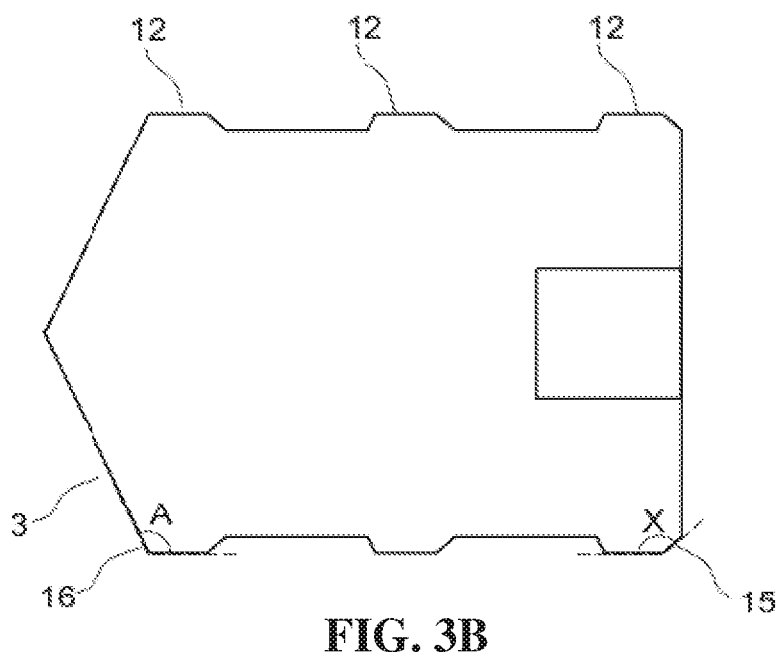
FIG. 3B illustrates a stopper as used according to an exemplary embodiment of this invention.

FIG. 3B shows a stopper 3 provided in accordance with an exemplary embodiment of this invention. The stopper has three annular protrusions 12, wherein the rising edge 15 of the most proximal annular protrusion and an inner surface of the barrel (not shown) will span angle X in the distal direction, and the falling edge 16 of the most distal annular protrusion and the inner surface span angle A in the proximal direction, when this stopper is disposed in a barrel of the pharmaceutical container. The ratio X/A is at least 1.05.

Figure 4:
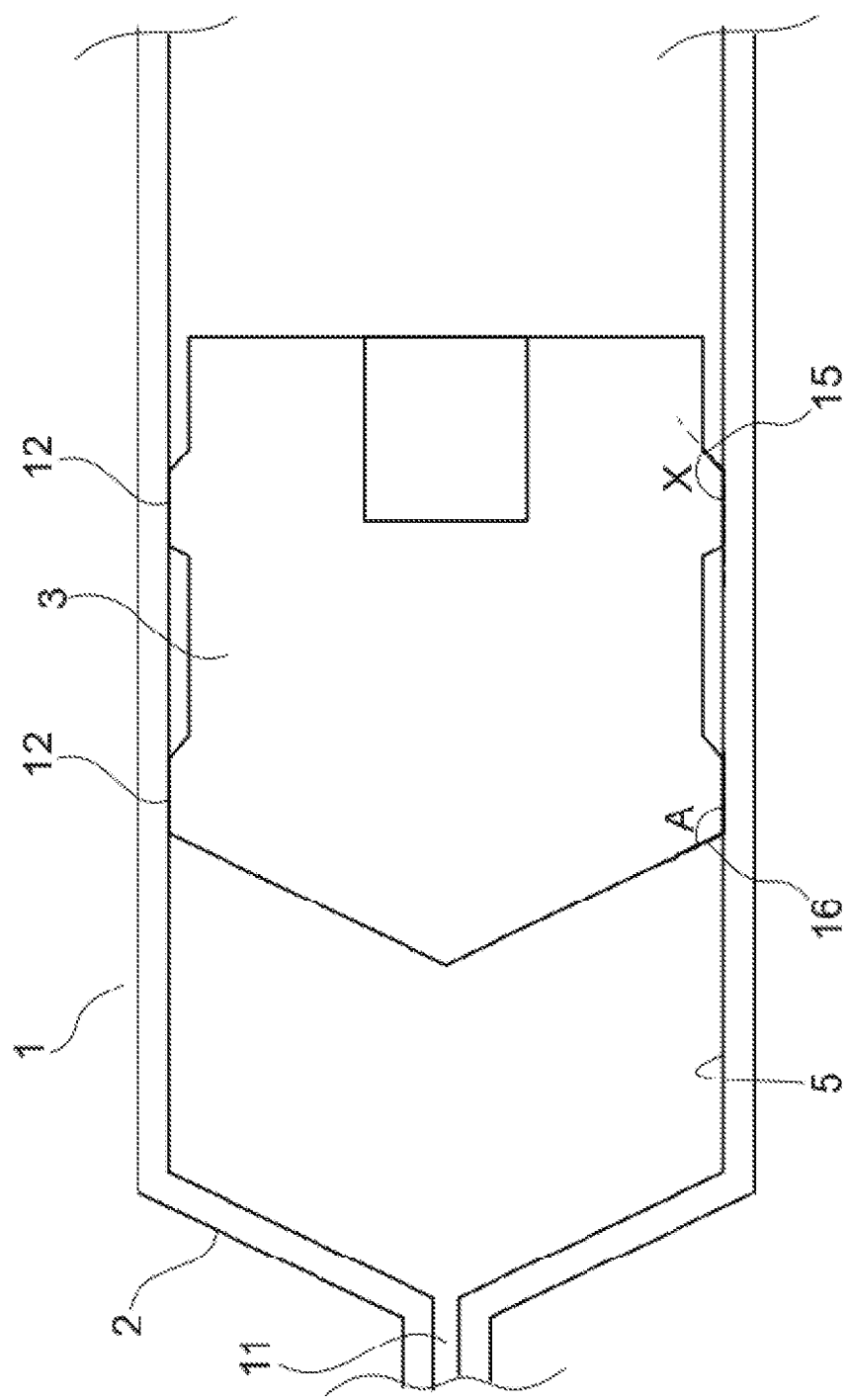
FIG. 4 illustrates a pharmaceutical container comprising a stopper, provided according to an exemplary embodiment of this invention.

FIG. 4 shows a pharmaceutical container 1 provided in accordance with an exemplary embodiment of the invention. The pharmaceutical container has an inner surface 5 and a stopper 3 being slidably arranged within the barrel 2. The stopper has two annual protrusions 12, wherein rising edge 15 of the most proximal annular protrusion and inner surface 5 of barrel 2 span angle X in the distal direction, and falling edge 16 of the most distal annular protrusion and inner surface 5 span angle A in the proximal direction. The ratio X/A is at least 1.05. The figure also shows outlet 11.

Examples

Tests were performed using pharmaceutical containers of 1 ml volume with stoppers 1 to 3 and comparative stopper 4, which is an example of a stopper from WO 2018/157097 A1. All containers used for the tests had uncoated inner surfaces.

The containers to be tested were filled with water for injection or demineralized water. They were fixed in vertical orientation in a universal testing machine model 106, 2 kN from TesT AG, CH-6331 Hünenberg, Switzerland. The universal testing machine pushed the stoppers with a speed of 20 mm/min into the containers until an initial force of 0.25 N is reached. Thereafter, the stoppers are pushed with a test speed of 100 mm/min into the containers and the force is recorded until a shut-off value of 35 N is reached.

TABLE 1

| BLGF Tests | | | | |
|---|---|---|---|---|
| # | BLF [N] | avg. GF [N] | TGFV | BLF/GF |
| Stopper 1 | 1.9 | 1.5 | 0.6 | 1.2 |
| Stopper 2 | 2.2 | 1.9 | 1.5 | 1.16 |
| Stopper 3 | ./. | ./. | ./. | ./. |
| Stopper 4 | 9.6 | 6.6 | ./. | 1.45 |

Figure 5:
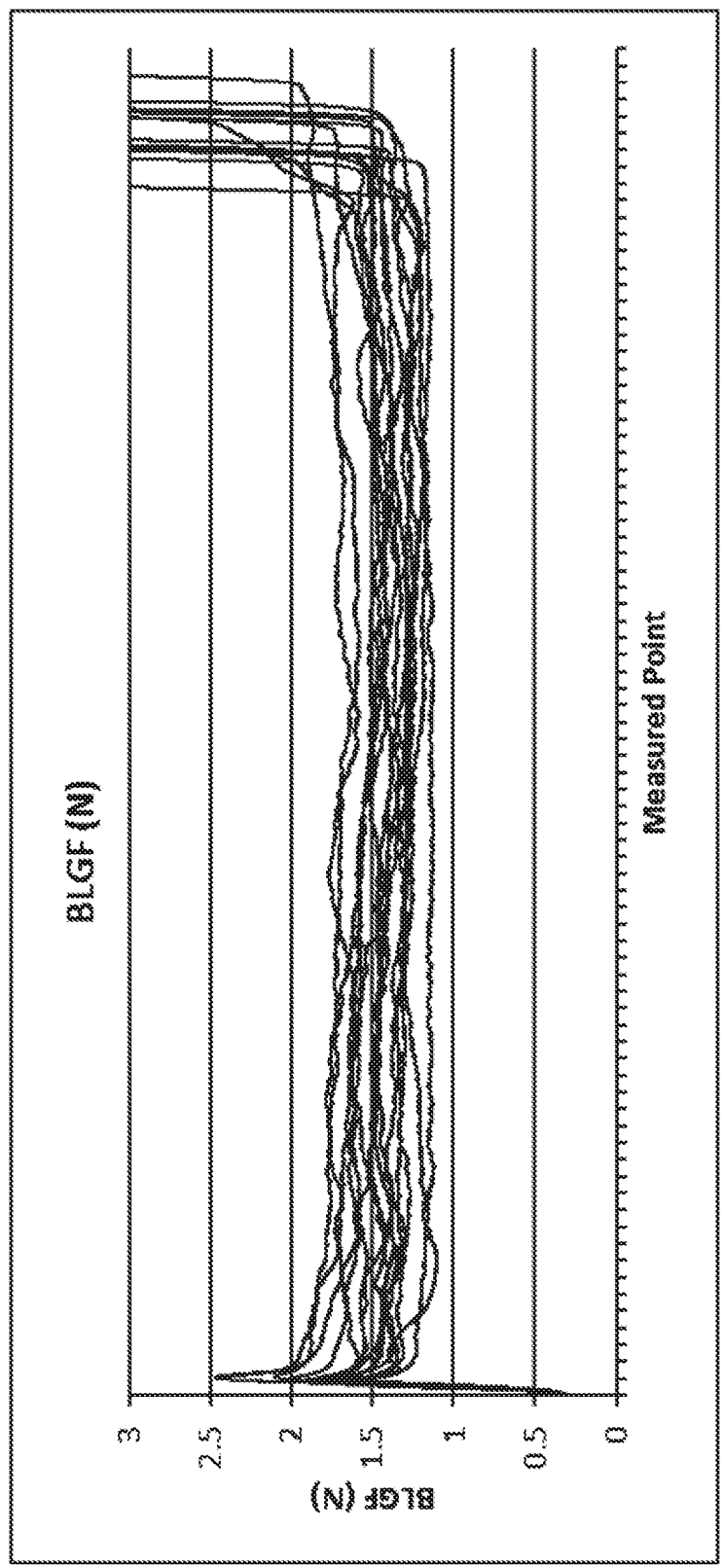
FIG. 5 illustrates a BLGF diagram for an exemplary embodiment of a pharmaceutical container provided according to this invention.
Figure 6:
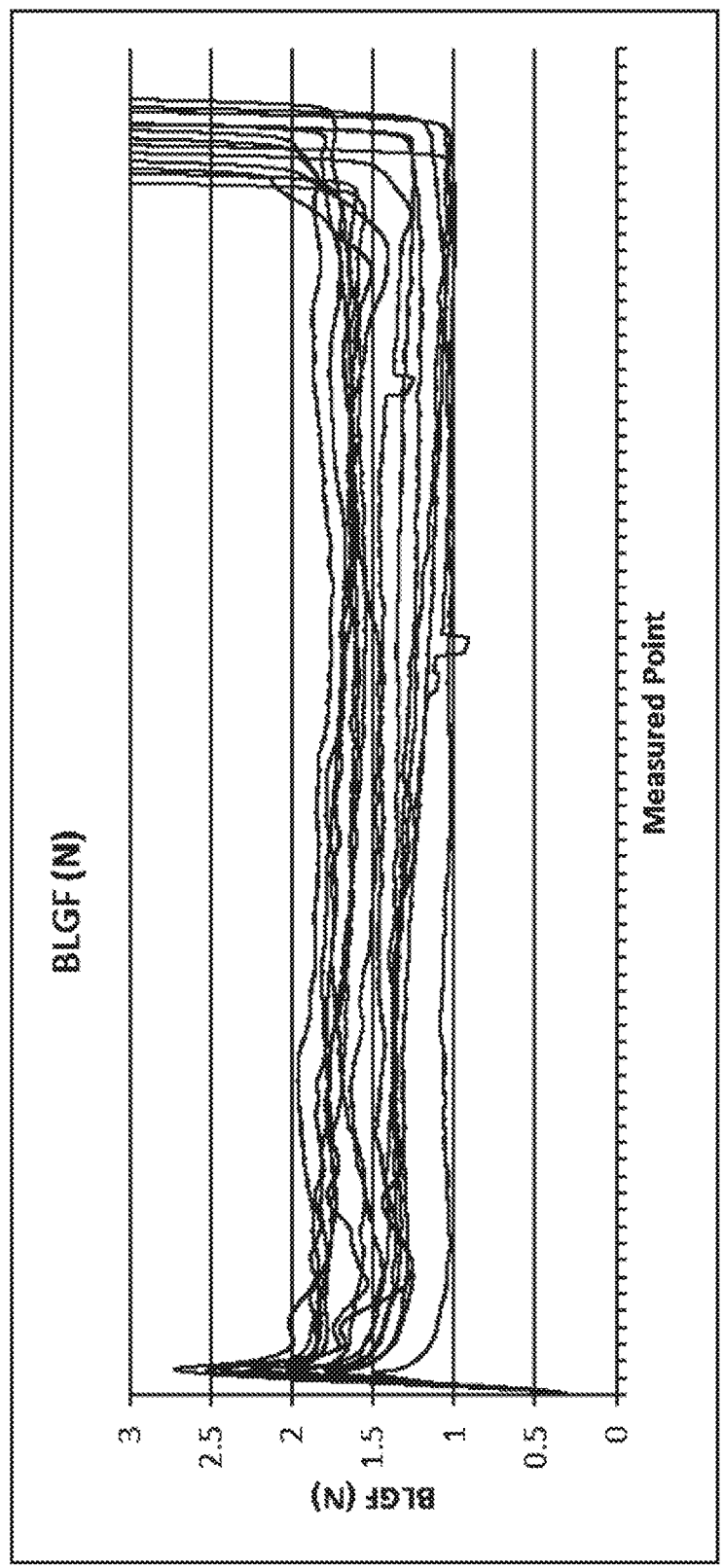
FIG. 6 illustrates a BLGF diagram for the pharmaceutical container of FIG. 5 after 105 days of accelerated aging.

The results for stopper 1 are illustrated in FIG. 5. FIG. 6 shows that, even after accelerated aging, the values are still excellent.

Figure 7:
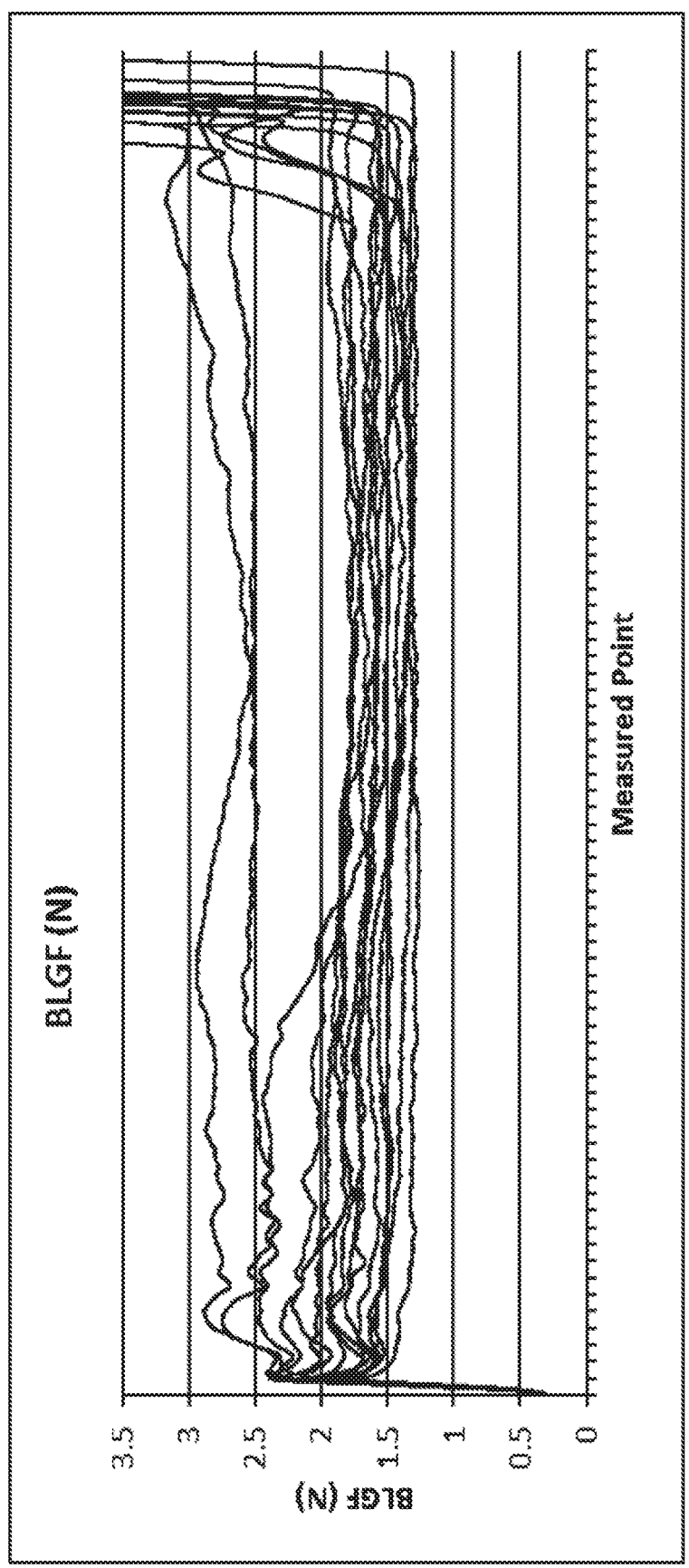
FIG. 7 illustrates a BLGF diagram for an exemplary embodiment of a pharmaceutical container provided according to this invention.
Figure 8:
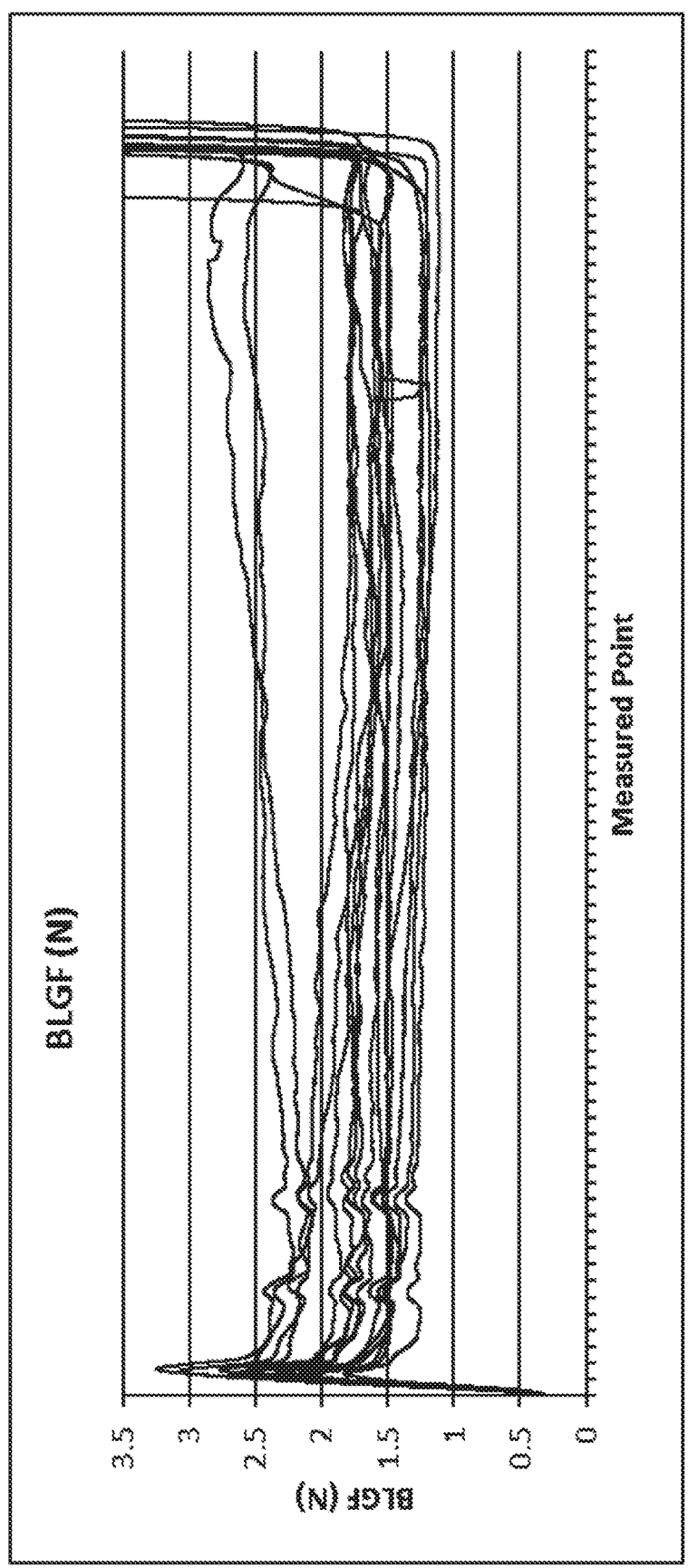
FIG. 8 illustrates a BLGF diagram for the pharmaceutical container of FIG. 7 after 105 days of accelerated aging.

The results for stopper 2 are illustrated in FIG. 7. FIG. 8 shows that, even after accelerated aging, the values are still excellent.

Roughness Values

Surface roughness values were obtained of the inner surfaces of the barrels used in examples 1 to 3. The results are given in the following table. All the barrels were uncoated.

| Barrel location | Rms [nm] | Ra [nm] |
|---|---|---|
| proximal | 79 | 62 |
| middle | 40 | 27 |
| distal | 19 | 14 |

The surface roughness values were measured with a white light interferometer according to DIN EN ISO 25178-2:2012, DIN EN ISO 25178-6:2010 and DIN EN ISO 25178-604:2013-12 (together with DIN EN ISO 4288:1998 and DIN EN ISO 3274:1998).

Dye Ingress Test

A dye ingress test was performed for a set of 15 aged and 15 non-aged samples. The test conditions were as follows.

Preparation of the Test Samples

The syringes to be tested are filled with water up to the nominal volume after their tips have been closed. Then the plunger stoppers are carefully inserted leaving 2-5 mm of air in the syringes. Syringes having already liquid between the sealing protrusions are to be discarded from the test.

Test Procedure

A desiccator is filled with fluorescein sodium salt solution and the prepared syringes are placed into the solution. Then the syringes are covered with a perforated lid in order to ascertain full immersion of the syringes in the solution. Thereafter, the desiccator is closed and connected to a vacuum pump (e.g. a type PC2001 Vario [brand no. 29951114-299512] from Vacuubrand GmbH & Co. KG, CH-8484 Theilingen, Switzerland). The desiccator is held for 30 min at a pressure of 270 mbar below atmospheric pressure. Thereafter, the desiccator is vented to atmospheric pressure and the syringes are left for another 30 min in the solution. Finally, the syringes are removed from the solution, carefully rinsed with water, dried with a lint free cloth, and inspected visually under UV light. The result of the visual inspection is recorded as passed or not passed. In case of failure the position of the leakage is also documented.

|  | non-aged (0 d) | aged (105 d) |
|---|---|---|
| Stopper 1 | passed | passed |
| Stopper 2 | passed | passed |

The results show that the pharmaceutical containers provided according to the invention provide for a tight seal of stopper and inner surface of the barrel even after accelerated aging for 105 days.

Axial Compression

An axial compression test was performed for a set of 15 aged and 15 non-aged samples. The test conditions were as follows. The syringes to be tested were filled with water, closed and fixed in vertical orientation in a universal testing machine model 106, 2 kN from TesT AG, CH-6331 Hünenberg, Switzerland. With the universal testing machine a pressure of 2.5 bar was exerted for 30 s on the plungers. Thereafter the syringes were visually inspected for water droplets having formed between the sealing protrusions and the results were recorded as passed or not passed.

|  | non-aged (0 d) | aged (105 d) |
|---|---|---|
| Stopper 1 | passed | passed |
| Stopper 2 | passed | passed |

The results show that the pharmaceutical containers provided according to the invention pass the axial compression test even after accelerated aging for 105 days.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A pharmaceutical container for drug delivery, comprising:
a barrel configured to slidably receive a stopper, the pharmaceutical container exhibiting a ratio of a break loose force (BLF) relative to a glide force (GF) of BLF/GF≤2 during a break loose and glide force test and a total glide force variation $TGFV=GF_{max}-GF_{min}$ measured when the stopper is moved from a start position to its end position is TGFV<2 N, the stopper having a proximal end suitable for contacting a plunger rod, a distal end suitable for contacting a pharmaceutical composition, a circumferential surface at least partially suitable for contacting an inner surface of the barrel, and one or more annular protrusions contacting the inner surface of the barrel when the stopper moves in a distal direction, the one or more annular protrusions each having a rising edge and a falling edge in a proximal-distal direction, the rising edge of a most proximal annular protrusion and the inner surface of the barrel span angle X in the distal direction, the falling edge of a most distal annular protrusion and the inner surface span an angle A in a proximal direction, and the ratio X/A is at least 1.05, wherein the stopper has a circumferential surface with a water contact angle $\theta c$ and the inner surface of the barrel has a water contact angle $\theta_I$, wherein a ratio of $\theta_C/\theta_I>0.9$.

2. The pharmaceutical container of claim 1, wherein the ratio X/A is from >1.1 to 1.7.

3. The pharmaceutical container of claim 1, wherein A is from 130° to 170°.

4. The pharmaceutical container of claim 1, wherein the stopper has at least two annular protrusions.

5. The pharmaceutical container of claim 1, wherein the pharmaceutical container is selected from the group consisting of a syringe, a cartridge and a carpule.

6. The pharmaceutical container of claim 1, wherein the inner surface of the barrel has a water contact angle of at least 80°.

7. The pharmaceutical container of claim 1, wherein the inner surface of the barrel has at least one of:
a surface roughness Ra of less than 100 nm;
a surface roughness Rms of less than 150 nm;
a surface energy of less than 45 mN/m; or
a silicone content of less than 100 μg per barrel.

8. The pharmaceutical container of claim 1, wherein the stopper is coated with a polymer selected from the group consisting of polytetrafluoroethylene (PTFE), densified expanded polytetrafluoroethylene (ePTFE), tetrafluoroethylene (TFE), tetrafluoroethylene-perfluoroethylene copolymer, tetrafluoroethylene-hexafluoropropylene copolymer, tetrafluoroethylene-ethylene copolymer, trichlorotrifluoroethylene, poly-vinylidene fluoride, polyvinyl fluoride, perfluoropropylvinylether, and perfluoroalkoxy polymers, as well as copolymers, blends and combinations thereof.

9. The pharmaceutical container of claim 1, wherein the ratio of the break loose force (BLF) relative to the glide force (GF) is BLF/GF≤3 after accelerated aging for 105 days.

10. The pharmaceutical container of claim 1, the pharmaceutical container exhibiting a maximum break loose and glide force of not more than 12 N during a break loose and glide force test.

11. The pharmaceutical container of claim 1, wherein a surface roughness of the inner surface of the barrel declines from the stopper's start position to its end position by at least 3% of at least one of Ra roughness or Rms roughness.

12. The pharmaceutical container of claim 1, wherein the stopper has a stopper compression SC of less than 0.1, wherein SC=(OD−ID)/OD, OD is equal to an outer diameter of the stopper, and ID is equal to an inner diameter of the barrel.

13. The pharmaceutical container of claim 1, wherein the barrel is partially or entirely made of glass or a polymer.

14. The pharmaceutical container of claim 1, wherein the inner surface of the barrel is uncoated.

15. The pharmaceutical container of claim 1, further comprising a liquid composition contained within the barrel.

16. The pharmaceutical container of claim 15, wherein the liquid composition comprises an active ingredient comprising at least one of a peptide, a protein, an antibody, an enzyme, a vaccine, a receptor, an immune inhibitory agent, an anti-cancer agent, an immune checkpoint inhibitor, or a TNFα antibody.

17. The pharmaceutical container of claim 1, further comprising the stopper slidably received in the barrel.

18. A pharmaceutical container for drug delivery, comprising:
   a barrel configured to slidably receive a stopper, the pharmaceutical container exhibiting a ratio of a break loose force (BLF) relative to a glide force (GF) of BLF/GF≤2 during a break loose and glide force test and a total glide force variation TGFV=$GF_{max}$−$GF_{min}$ measured when the stopper is moved from a start position to its end position is TGFV<2 N, wherein the stopper has a circumferential surface with a water contact angle $\theta_C$ and an inner surface of the barrel has a water contact angle $\theta_I$, wherein a ratio of $\theta_C/\theta_I$>0.9.

19. A method of treatment, comprising:
administering to a subject an effective amount of an active ingredient using a pharmaceutical container, the pharmaceutical container comprising:
   a barrel configured to slidably receive a stopper, the container exhibiting a ratio of a break loose force (BLF) relative to a glide force (GF) of BLF/GF≤2 during a break loose and glide force test and a total glide force variation TGFV=$GF_{max}$−$GF_{min}$ measured when the stopper is moved from a start position to its end position is TGFV<2 N, the stopper having a proximal end suitable for contacting a plunger rod, a distal end suitable for contacting a pharmaceutical composition, a circumferential surface at least partially suitable for contacting an inner surface of the barrel, and one or more annular protrusions contacting the inner surface of the barrel when the stopper moves in a distal direction, the one or more annular protrusions each having a rising edge and a falling edge in a proximal-distal direction, the rising edge of a most proximal annular protrusion and the inner surface of the barrel span angle X in the distal direction, the falling edge of a most distal annular protrusion and the inner surface span an angle A in a proximal direction, and the ratio X/A is at least 1.05, wherein the stopper has a circumferential surface with a water contact angle $\theta_C$ and the inner surface of the barrel has a water contact angle $\theta_I$, wherein a ratio of $\theta_C/\theta_I$>0.9.

20. A pharmaceutical container for drug delivery, comprising:
   a barrel configured to slidably receive a stopper, the pharmaceutical container exhibiting a ratio of a break loose force (BLF) relative to a glide force (GF) of BLF/GF≤2 during a break loose and glide force test and a total glide force variation TGFV=$GF_{max}$−$GF_{min}$ measured when the stopper is moved from a start position to its end position is TGFV<2 N, the stopper having a proximal end suitable for contacting a plunger rod, a distal end suitable for contacting a pharmaceutical composition, a circumferential surface at least partially suitable for contacting an inner surface of the barrel, and one or more annular protrusions contacting the inner surface of the barrel when the stopper moves in a distal direction, the one or more annular protrusions each having a rising edge and a falling edge in a proximal-distal direction, the rising edge of a most proximal annular protrusion and the inner surface of the barrel span angle X in the distal direction, the falling edge of a most distal annular protrusion and the inner surface span an angle A in a proximal direction, and the ratio X/A is at least 1.05, wherein the stopper has a stopper compression SC of less than 0.1, wherein SC=(OD-ID)/OD, OD is equal to an outer diameter of the stopper, and ID is equal to an inner diameter of the barrel.

21. A pharmaceutical container for drug delivery, comprising:
   a barrel configured to slidably receive a stopper, the pharmaceutical container exhibiting a ratio of a break loose force (BLF) relative to a glide force (GF) of BLF/GF≤2 during a break loose and glide force test and a total glide force variation TGFV=$GF_{max}$−$GF_{min}$ measured when the stopper is moved from a start position to its end position is TGFV<2 N, wherein the stopper has a stopper compression SC of less than 0.1, wherein SC=(OD-ID)/OD, OD is equal to an outer diameter of the stopper, and ID is equal to an inner diameter of the barrel.

22. A method of treatment, comprising:
administering to a subject an effective amount of an active ingredient using a pharmaceutical container, the pharmaceutical container comprising:
   a barrel configured to slidably receive a stopper, the container exhibiting a ratio of a break loose force (BLF) relative to a glide force (GF) of BLF/GF≤2 during a break loose and glide force test and a total glide force variation TGFV=$GF_{max}$−$GF_{min}$ measured when the stopper is moved from a start position to its end position is TGFV<2 N, the stopper having a proximal end suitable for contacting a plunger rod, a distal end suitable for contacting a pharmaceutical composition, a circumferential surface at least partially suitable for contacting an inner surface of the barrel, and one or more annular protrusions contacting the inner surface of the barrel when the stopper moves in a distal direction, the one or more annular protrusions each having a rising edge and a falling edge in a proximal-distal direction, the rising edge of a most proximal annular protrusion and the inner surface of the barrel span angle X in the distal direction, the falling edge of a most distal annular protrusion and the inner surface span an angle A in a proximal direction, and the ratio X/A is at least 1.05, wherein the stopper has a stopper compression SC of less than 0.1, wherein SC=(OD-ID)/OD, OD is equal to an outer diameter of the stopper, and ID is equal to an inner diameter of the barrel.

* * * * *